United States Patent
Li et al.

(10) Patent No.: US 8,064,676 B2
(45) Date of Patent: Nov. 22, 2011

(54) VIRTUAL GRID IMAGING METHOD AND SYSTEM FOR ELIMINATING SCATTERED RADIATION EFFECT

(75) Inventors: Yunxiang Li, Beijing (CN); Hongguang Cao, Beijing (CN)

(73) Assignee: Beijing Sinopharm Hundric Medline Info. Tec. Co. Ltd., Beijing (CN)

( * ) Notice: Subject to any disclaimer, the term of this patent is extended or adjusted under 35 U.S.C. 154(b) by 416 days.

(21) Appl. No.: 12/514,541

(22) PCT Filed: Jun. 8, 2007

(86) PCT No.: PCT/CN2007/001817
§ 371 (c)(1),
(2), (4) Date: May 12, 2009

(87) PCT Pub. No.: WO2008/058442
PCT Pub. Date: May 22, 2008

(65) Prior Publication Data
US 2010/0046822 A1 Feb. 25, 2010

(30) Foreign Application Priority Data
Nov. 14, 2006 (CN) .......................... 2006 1 0114533

(51) Int. Cl.
*G06K 9/00* (2006.01)
(52) U.S. Cl. ........................................................ 382/132
(58) Field of Classification Search ................ None
See application file for complete search history.

(56) References Cited

U.S. PATENT DOCUMENTS

| 5,278,754 | A | 1/1994 | Arakawa |
| 6,687,326 | B1 | 2/2004 | Bechwati et al. |
| 6,973,158 | B2 * | 12/2005 | Besson ........................... 378/16 |
| 2004/0264626 | A1 * | 12/2004 | Besson ........................... 378/4 |
| 2005/0025278 | A1 | 2/2005 | Hagiwara |
| 2005/0147200 | A1 | 7/2005 | Nukui |

FOREIGN PATENT DOCUMENTS

| CN | 1 577 076 A | 2/2005 |
| CN | 1 596 828 A | 3/2005 |
| CN | 1 636 516 A | 7/2005 |
| EP | 1 516 588 A1 | 3/2005 |

* cited by examiner

*Primary Examiner* — Tu Nguyen
(74) *Attorney, Agent, or Firm* — Birch, Stewart, Kolasch & Birch, LLP

(57) ABSTRACT

A virtual grid imaging method capable of eliminating scattered radiation effect and an imaging system thereof for imaging with high energy rays, in which scattered rays reaching a surface of a detector are not filtered, and data of the scattered rays and straight rays are all sampled. The method includes decomposing a digital image into multi-band images from high to low according to frequencies; performing de-scattering process for low-frequency band images; performing contrast enhancement process for high-frequency band images; and merging the images of various frequency bands processed in the second and third steps, and forming an output image. In digital X-ray imaging the scattered radiation effect is eliminated. Significant reduction of the dosage of the rays, in which only one third of the required dosage of a common grid is used to obtain the same image brightness.

13 Claims, 6 Drawing Sheets

VIRTUAL GRID IMAGING METHOD AND SYSTEM FOR ELIMINATING SCATTERED RADIATION EFFECT

BACKGROUND OF THE INVENTION

1. Field of the Invention

The present invention relates to a virtual grid imaging method for eliminating scattered radiation effect and an imaging system thereof, and more particularly to a virtual grid imaging method and imaging system thereof capable of eliminating scattered radiation effect generated by high energy rays such as X-rays and gamma rays after passing through a to-be-detected object, which belongs to the field of digital image processing technology.

2. Description of Related Art

High energy rays including X-rays and gamma rays have a strong penetration power, capable of penetrating through many substances opaque to visible lights, such as inking sheet and timber. With this penetration power, the high energy rays are used to perform medical diagnosis and treatment, used to test nondestructive materials in industry, and widely used to analyze crystal structure and perform chemical analysis and researches on atomic structure through spectrum and absorption situation of the rays in the fundamental science and applied sciences.

When irradiating the to-be-detected object with high energy rays, after the rays penetrate through the to-be-detected object, not only primary radiation is generated, but scattered radiation is also generated. The scattered radiation generates extra exposure, which overlaps on the image of the rays as a "scattering fog", thereby reducing the contrast and definition of the image of the rays, and reducing the noise-to-signal ratio at details of the image. The specific reducing degree depends on the intensity of the scattered radiation.

In order to alleviate adverse effects caused by the scattered radiation, several technical solutions have been researched. Taking the most commonly-used X-rays for an example, a special anti-scatter grid has been generally used at home and abroad. This type of anti-scatter grid is referred to as a grid, which is published by U.S. Pat. No. 1,164,987 the earliest. The grid is disposed between the to-be-detected object and an X-ray detector, allows the primary radiation from a focal point of the X-ray tube to pass through, but substantially absorbs scattered radiation from the to-be-detected object and incident in different angles. The grid is generally made of lead with a small volume and a high absorptivity. A medium between the absorbers is paper, fiber, aluminum, or a kind of inelastic foam with a high resistance. The latest technical development for the grid can be obtained with reference to documents such as Chinese Patent Application, entitled "Anti-scatter Grids for X-ray Equipments" (Application Number: 02126906.8, Date of Publication: Apr. 2, 2003).

With the anti-scatter gird, the scattered radiation generated in the to-be-detected object is reduced and the imaging quality is improved, however, the anti-scatter gird itself also blocks a portion of the X-rays that should be incident to the X-ray detector. In order to alleviate the adverse effects, the radiation dosage of the X-rays must be increased, which causes disadvantages in two aspects. In one aspect, the to-be-detected object, particularly patients and medical workers, suffers from an increased radiation, and in the other aspect, the requirements for the X-ray tube and high-voltage generator are increased, thereby the manufacturing cost of the X-ray detecting apparatus is increased.

In Chinese Patent Application, entitled "Anti-scatter X-ray Shielding used in CT Scanner" (Application Number: 02829542.0, Date of Publication: Sep. 21, 2005), an anti-scatter (AS) material used for absorbing X-rays between X-ray detector rows, and an AS material used for absorbing X-rays between X-ray detector columns are provided, in which the AS materials are respectively located between every two rows/columns of detectors. Furthermore, the thickness and/or height of the foil between rows can be different from the thickness and/or height of the foil between columns. Moreover, in Chinese Patent Application, entitled "Incoherent Scattering Eliminating Device Used in X-ray Phase Imaging Based on Energy Recognition" (Application Number: 200610024489.1, Date of Publication: Aug. 23, 2006), an incoherent scattering eliminating device used in X-ray phase imaging based on energy recognition is provided, which includes three parts: an X-ray generation and modulation system, a to-be-detected object fixing device, and a back-end X-ray modulation and detection system. This invention selects different filtering materials, and ensures that substantially no loss occurs in the valid X-rays, and almost all the primary radiation with a constant wavelength reach the X-ray detector, thereby eliminating the influences to the imaging quality caused by the incoherent scattering.

SUMMARY OF THE INVENTION

The present invention is directed to a "virtual grid" imaging method capable of effectively eliminating scattered radiation effect. In this method, scattered rays reaching a surface of a detector are not filtered, data of the scattered rays and straight rays are all sampled, and then, separation and inhibition of scattered ray component are performed for the sampled data, thereby eliminating the scattered ray component in the resulted image.

The present invention is further directed to an imaging system for realizing the above "virtual grid" imaging method.

In order to achieve the above objectives, the present invention adopts the following technical solutions.

A virtual grid imaging method for eliminating scattered radiation effect, applicable for imaging with high energy rays, is provide, which includes the following steps:

(1) decomposing a digital image generated by high energy rays into multi-band images from high to low according to frequencies;

(2) directly performing de-scattering process for low-frequency band images;

(3) performing contrast enhancement process for high-frequency band images;

(4) merging the images of various frequency bands after being processed in the step (2) and the step (3), and forming an output image.

In the step (1), the digital image is decomposed by means of Laplacian Pyramid decomposition.

Alternatively, in the step (1), the digital image is decomposed by means of Wavelet Transform.

In the step (1), the number n of layers decomposed from the digital image meets the following equation:

$$n = \log(N)/\log(2) - 0.5,$$

wherein N is the size of the digital image.

In the step (2), the de-scattering process is performed for the low-frequency band images according to the following equation:

$$C_k(x,y) = \text{Gain}(L_k(x,y),k) \times L_k(x,y)$$

wherein $\text{Gain}(L_k(x,y),k) \in [0,1]$ is a function in positive correlation with image brightness and frequency band, $C_k(x,y)$ is the low-frequency band images after being processed, $L_k(x,y)$ is the low-frequency band images obtained from decomposition in the step (1), and K is a positive integer.

In the step (3), the contrast enhancement process is performed for the high-frequency band images according to the following equation:

$$E_k(x,y)=\text{Sigm}(L_k(x,y),k) \times L_k(x,y),$$

wherein $\text{Sigm}(L_k(x,y),k)$ is an S-type nonlinear amplification function, in inverse correlation with contrast of pixel, $E_k(x,y)$ is the high-frequency band images after being processed, $L_k(x,y)$ is the high-frequency band images obtained from decomposition in the step (1), and K is a positive integer.

In the step (4), first, an interpolation frequency up-conversion sampling is performed for the lowest frequency band image after being processed in the step (2), and then, the image is overlapped with an adjacent image of a higher frequency band through Gaussian Convolution interpolation process, so as to generate a new image of a higher frequency band, and the same process is performed upwards layer by layer, until a processed image of a size identical to the original image is obtained.

In the step (4) or after the step (4), a de-noising process is performed for the image according to the following equation:

$$f_k(x,y)=(1-b) \times R_k(x,y)+b \times T_{k+1}(x,y),$$

wherein $b=\text{Weight}(T_{k+1}(x,y),k)$ is in positive correlation with image brightness and frequency band, $R_k(x,y)$ is an image of a certain frequency band, $T_{k+1}(x,y)$ is a image of a lower frequency band after performing the interpolation frequency up-conversion sampling process, and $f_k(x,y)$ is the image of the frequency band output after performing de-noising process.

The data required during the image processing is compiled in advance, and corresponding mapping curves are fitted, such that when performing the image processing, the required data can be obtained quickly by directly using a mapping process through a lookup table.

The high energy rays include, but not limited to, X-rays or gamma rays.

A virtual grid imaging system for eliminating scattered radiation effect is provided, which is characterized in that:

the virtual grid imaging system includes a high energy ray emitting unit, a high energy ray detecting unit, an imageacquiring, pre-processing and correcting unit, a virtual grid unit, an image post-processing unit, and an image displaying unit. The high energy ray emitting unit emits high energy rays that penetrate through the to-be-detected object and then received by the high energy ray detecting unit to generate a digital image. The high energy ray detecting unit, the imageacquiring, pre-processing and correcting unit, the virtual grid unit, the image post-processing unit, and the image displaying unit are connected in sequence, and after the virtual grid unit performs the above virtual grid processing process, the image with the scattered radiation effect being eliminated is sent to the image displaying unit to be displayed.

The high energy ray emitting unit is an X-ray tube, and the high energy ray detecting unit is an X-ray detector.

The virtual grid imaging method and system thereof realized in the present invention can effectively eliminate the influences for the resulted digital image caused by scattered radiation generated in the to-be-detected object. In digital X-ray imaging, as for the images having been influenced by the scattered radiation, the "scattering fog" overlapped on the X-ray image is eliminated through the digital signal processing, thereby increasing the contrast and signal-to-noise ratio of the X-ray image. In addition, the X-ray image is obtained by using radiation dosage as low as possible, such that the X-ray radiation suffered by patients and medical workers is minimized.

Experiment proves that, in digital X-ray imaging, the present invention can obviously eliminate the scattered radiation effect, and meanwhile significantly reduce the ray dosage at the same time, in which only one third of the required dosage of the common grid is used for obtaining the same image brightness.

BRIEF DESCRIPTION OF THE DRAWINGS

The accompanying drawings are included to provide a further understanding of the invention, and are incorporated in and constitute a part of this specification.

DESCRIPTION OF EMBODIMENTS

A basic principle of the present invention lies in that, during the imaging process with high energy rays, for the images having been influenced by the scattered radiation, "scattering fog" overlapped on the ray image is eliminated by digital signal processing, so as to improve the contrast and signal-to-noise ratio of the high energy ray image. The high energy rays include, but not limited to, X-rays, gamma rays and etc. In the following embodiments, the illustration is made by taking the most commonly used X-rays as an example.

Figure 1:
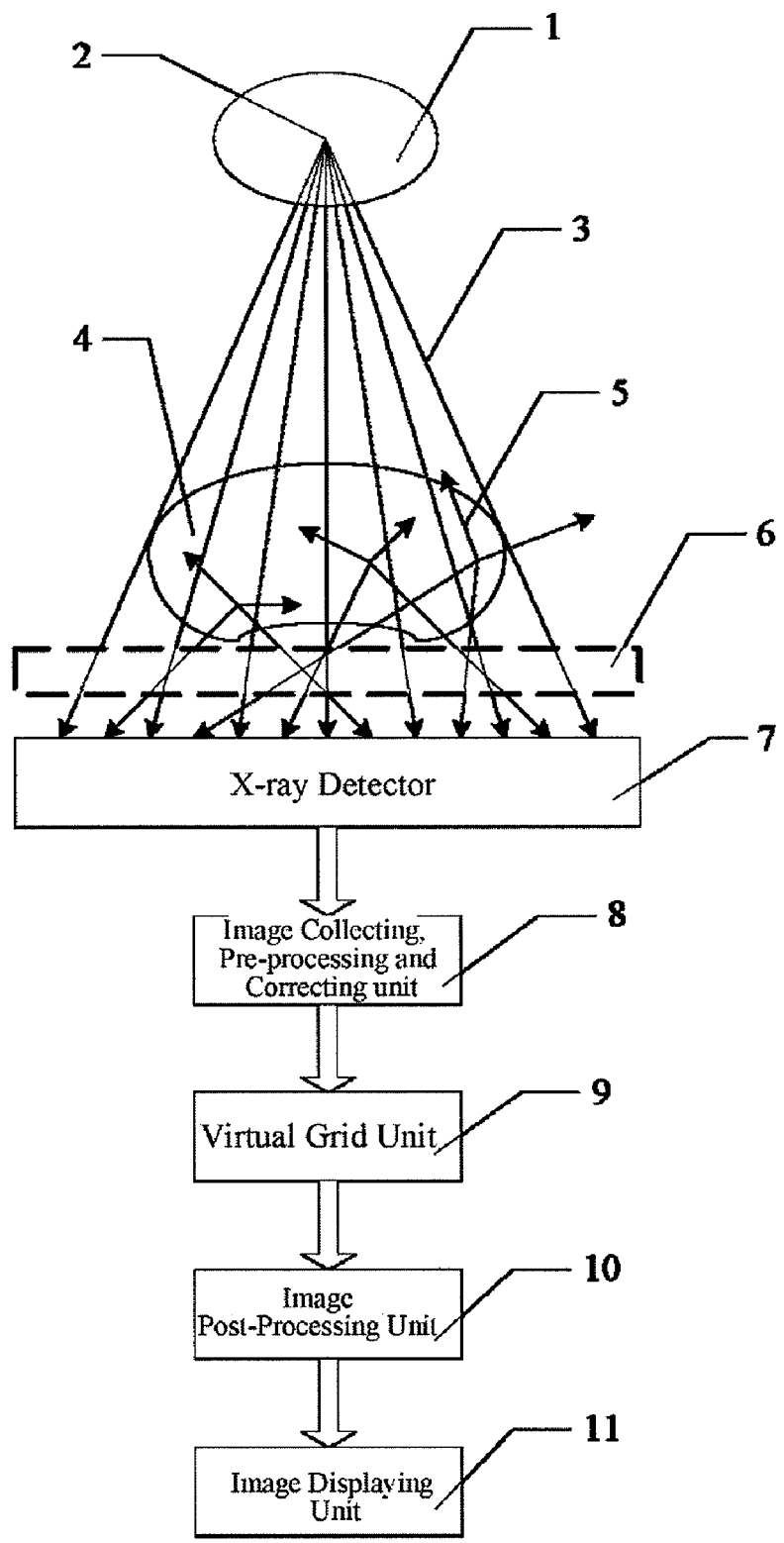
FIG. 1 is a schematic view of a virtual grid imaging system according to the present invention.

FIG. 1 shows an embodiment of the "virtual grid" imaging system according to the present invention. The system includes an X-ray tube 1 serving as a high energy ray emitting unit, an X-ray detector 7, an imageacquiring, pre-processing and correcting unit 8, a virtual grid unit 9, an image post-processing unit 10 and an image displaying unit 11. Referring to FIG. 1, an X-ray beam flow 3 is emitted from a focal point 2 of the X-ray tube 1, and irradiated to a to-be-detected object 4. The X-rays penetrating through the to-be-detected object 4 are straightly incident to the X-ray detector 7. Furthermore, scattered rays 5 generated in the to-be-detected object are also incident to the X-ray detector 7 randomly from different angles. In the prior art, in order to alleviate the adverse impact of "scattering fog" caused by the scattered rays 5, an anti-scatter grid 6 (shown by dashed lines in the figure) is generally disposed between the to-be-detected object 4 and the X-ray detector 7. As described above, this type of anti-scatter grid brings many side effects, and thus being not a preferred solution. In the present invention, the image acquired by the X-ray detector 7 is processed by an advanced digital signal processing technique, and particularly, the X-ray detector 7 converts both the incident straight X-rays and scattered rays into a digital signal for being processed by the imageacquiring, pre-processing and correcting unit 8, after that, the signal is decomposed into a straight X-ray signal and a scattered ray signal by the virtual grid unit 9, thereby eliminating the "scattering fog" formed on the image by the scattered rays. The X-ray image with the "scattering fog" being eliminated is further processed by the image post-processing unit 10, and then displayed on a monitor through the image displaying unit 11, for the relevant workers to make further researches. In this "virtual grid" imaging system, the virtual grid unit 9 is used to directly eliminate the impacts on the image quality caused by the X-ray scattering, such that the above anti-scatter grid 6 is no longer required. The X-ray dosage emitted from the X-ray tube 1 can be reduced correspondingly, thereby reducing the suffering to the medical workers and patients.

The work finished by the virtual grid unit 9 is the core of the present invention, and the specific working flow thereof is illustrated below in detail.

The virtual grid unit 9 executes an algorithm for eliminating scattered radiation effect specifically provided by the inventor of the present invention. The algorithm is based on the understanding of the following models.

1. "Scattering fog" Image Degradation Model:

$$g(x,y)=f(x,y)+s(x,y)+n(x,y) \quad (1),$$

wherein $g(x,y)$ is an X-ray image, $f(x,y)$ is an image generated by straight radiation, $s(x,y)$ is an image generated by the scattered radiation, $n(x,y)$ is an quantum noise. It can be seen from the model that, X-ray image is composed by straight image added with the "scattering fog" image and the quantum noise.

After research, the scattering image can be approximately presented by the straight image after being processed by Gaussian low-pass filter:

$$s(x,y) \approx A \times f(x,y)*G_\sigma(x,y) \quad (2),$$

wherein $G_\sigma(x,y)$ is a Gaussian Convolution kernel with a standard deviation of $\sigma$; A is gain, which is directly proportional to the thickness and density of the to-be-detected object.

In X-ray imaging, the rays attenuate exponentially, and the characteristics of the X-ray noise include:
 a. mainly distributed on low-dosage imaging areas;
 b. noises are mainly distributed on high-frequency band of images;
 c. noises are random in time and space.

2. Multi-band Image Model

The meaning of this model lies in that: the X-ray image is formed by overlapping layers of different frequencies from high to low, just like the sunlight is formed by overlapping seven color spectrums.

Figure 2:
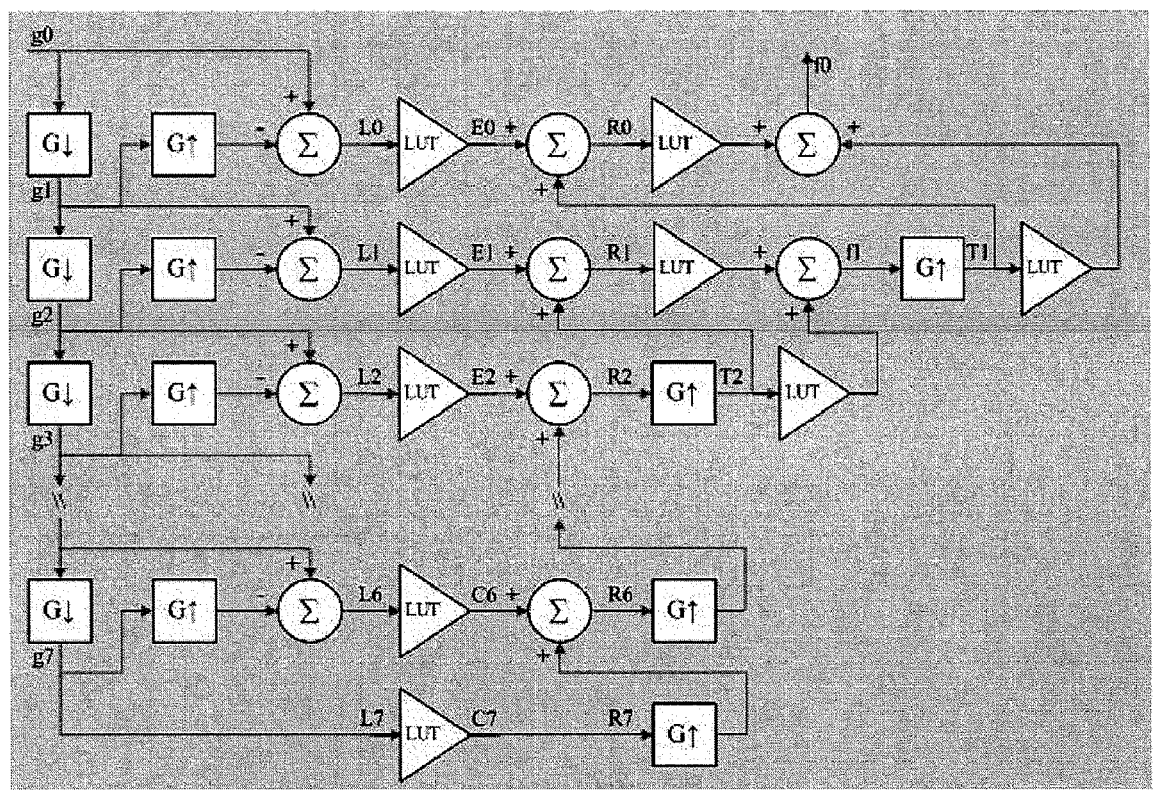
FIG. 2 is a flow chart of a virtual grid imaging method according to the present invention.

According to the above two models, as shown in the flow of virtual grid algorithm in FIG. 2, in the present invention, Laplacian Pyramid decomposition is used to decompose the image input by the X-rays into images under multiple scales, i.e., multi-band images with frequencies from high to low in sequence. Then, de-scattering processes of different extents are respectively performed for the low-frequency band images, and contrast enhancement process and de-noising process of different extents are respectively performed for the high-frequency band images. Then, the processed images under each scale are merged, so as to obtain a restored image for being output.

Particularly, the above "virtual grid" algorithm is divided into 4 sub-processes.

1. Image Decomposition Process

The X-ray image is decomposed by Laplacian Pyramid decomposition process. First, the input image g0 is processed by Gaussian low-pass filter and through interval sampling to obtain an image g1 with a half resolution:

$$g_{k+1}(x,y)=[g_k(x,y)*G_\sigma(x,y)](2x,2y) \quad (3),$$

wherein $G_\sigma(x,y)$ is a Gaussian convolution kernel with a standard deviation of $\sigma$, and K is a positive integer. In this embodiment, $\sigma=1$, the convolution kernel is 5×5, however, the convolution kernel can definitely be other numerals.

Then, the obtained g1 is frequency up-conversion sampled to restore the size of the original image, and the frequency up-conversion sampling is a process of interpolating 0 between sampling points:

$$g'_{k+1}(x,y) = \begin{cases} g_{k+1}(x/2, y/2) & x, y = 0, 2, 4... \\ 0 & x, y, = 1, 3, 5.... \end{cases} \quad (4)$$

After the frequency up-conversion sampling process, the image is processed by Gaussian convolution interpolation, and then, subtracted from the original image to obtain a first layer of differential image L0:

$$L_k(x,y)=g_k(x,y)-[g'_{k+1}(x,y)*G_\sigma(x,y)](x,y) \quad (5).$$

The above image decomposition is performed iteratively on the image after being processed by interval sampling, a group of $L_k(x,y)$ is obtained after n iterations, and the difference operation is not performed for the final low frequency image $g_{n-1}(x,y)$, and thus $L_{n-1}(x,y)=g_{n-1}(x,y)$. The series of images $L_k(x,y)$ are referred to as Laplacian image pyramid. The largest number of layers n of the image pyramid (i.e., times for decomposing the image) depends on the image size N:

$$n=\log(N)/\log(2)-0.5 \quad (6).$$

After the input image is decomposed into the Laplacian image pyramid, the images of each layer are corresponding to images of a different frequency band, in which L0 is the decomposed image of the highest frequency band, and $L_{n-1}(x,y)$ is the decomposed image of the lowest frequency band. In practice, the number of layers for the decomposed image is preferably 4~8, if it is too small, the scattered radiation effect is difficult to be eliminated, and if too large, the operations are too complicated to be used. In the embodiment shown in FIG. 2, it is illustrated by taking decomposing the image into 8 layers as an example.

2. De-scattering Process

According to the characteristics of the X-ray noises as described above, the images of different frequency bands are respectively processed through different methods. Low-frequency band images L7, L6, L5 and L4 are components in the image that are changed slowly, in which the scattering components of the image are mainly distributed. By means of weakening this part of components, the objective of eliminating the scattered rays can be achieved. Therefore, the weakening extents are sequentially reduced from L7 to L4, and the specific implementation is as follows:

$$C_k(x,y)=\text{Gain}(L_k(x,y),k) \times L_k(x,y) \quad (7),$$

wherein $\text{Gain}(L_k(x,y),k) \in [0,1]$ is a function of image brightness and frequency band, and the lower the brightness is, the smaller the function value is, and the lower the frequency band is, the smaller the function value is.

L7, L6, L5 and L4 are processed as that described above, so as to obtain corresponding C7, C6, C5 and C4.

It can be seen from the weakening process of the scattering components that, the weakening extent is relatively large in the area with relatively small image brightness, because the low-dosage imaging area has more scattered rays.

3. Enhancement Process

Due to the scattered rays existed in the imaging process, the contrast of the image is reduced, and thus the detailed parts of the image are blurred. In order to make the details of the image become clear, the enhancement process must be performed for the image, so as to increase the contrast of the image, which can be realized by the following equation:

$$E_k(x,y) = \text{Sigm}(L_k(x,y),k) \times L_k(x,y) \quad (8),$$

wherein $\text{Sigm}(L_k(x,y),k) > 1$, and it is an S-type nonlinear amplification function. Pixel with small contrast represent details of the image, and require a large amplification factor. The pixel with large contrast represent edges of the image, and require a small amplification factor, so as to avoid over-enhancement of the image. In addition, as the details of the image are mainly in high frequency bands, the amplification factor of the high-frequency band images must be larger than that of the middle frequency band images.

According to the above equation, the enhancement process is performed for L0, L1, L2 and L3, so as to obtain corresponding C0, C1, C2 and C3.

4. Image Merging Process

The image merging process refers to remerging images of different frequency bands after being processed by the de-scattering process and the enhancement process, so as to generate a new X-ray image, which includes the following steps.

The interpolation frequency up-conversion sampling is performed for R7 according to equation (4), such that the size of the image is expanded to twice thereof, so as to obtain $R_{k+1}'(x,y)$. Then, the Gaussian Convolution interpolation is performed, for being overlapped with C6, so as to obtain R6:

$$R_k(x,y) = C_k(x,y) + [R'_{k+1}(x,y) * G_\sigma(x,y)](x,y) \quad (9).$$

The same process is performed upwards layer by layer according to this method, and thus the processed image of a size identical to the original image is obtained.

A typical algorithm embodiment for realizing virtual grid has been illustrated above. In this embodiment, the X-ray image is decomposed by Laplacian Pyramid decomposition algorithm based on Gaussian Pyramid decomposition. However, it is obvious that the X-ray image can also be decomposed by other processes, such as direct sampling pyramid algorithm, and Wavelet Transform. As for this point, it can be obtained with reference to "Image Engineering (I): Image Processing (2nd)" (ISBN 7-302-12445-0/TN•301), edited by Zhang Yu-Jin, especially Chapter 14 "multi-scale image technique", which is not repeatedly described herein.

With the method provided by the present invention, the process of eliminating scattered ray effect is the same as that described in the above embodiment and substantially the same result can be achieved, no matter which specific image decomposition algorithm is used.

During the X-ray imaging process, interference of noises widely exists. The noises are distributed randomly in the high frequency bands of the image, and in the area of low-dosage imaging, the interference of noises is much larger. In the other aspect, the above detail enhancement process also amplifies the noises. In order to further inhibit the noises, and increase the signal-to-noise ratio of the image, de-noising process must be performed for the image.

The de-noising process can be performed separately, and can also be performed together with the merging process of the image. The specific de-noising algorithm is as follows.

$$f_k(x,y) = (1-b) \times R_k(x,y) + b \times T_{k+1}(x,y) \quad (10),$$

$$b = \text{Weight}(T_{k+1}(x,y),k) \quad (11),$$

wherein $b \in [0,1]$, and represents the de-noising extent, and it is a function of the image brightness and the frequency band, in which the lower the brightness is, the higher the function value is, and the higher the frequency band is, the high the function value is.

When performing the de-noising process in practice, it is not necessary to take the same de-noising measure for all the frequency bands, as in low frequency bands, the impact of the noises are small and can be ignored. Therefore, in the embodiment shown in FIG. 2, the above de-noising process is performed only for the two highest frequency bands, in which f0 is the output image after the de-noising process.

Figure 3:
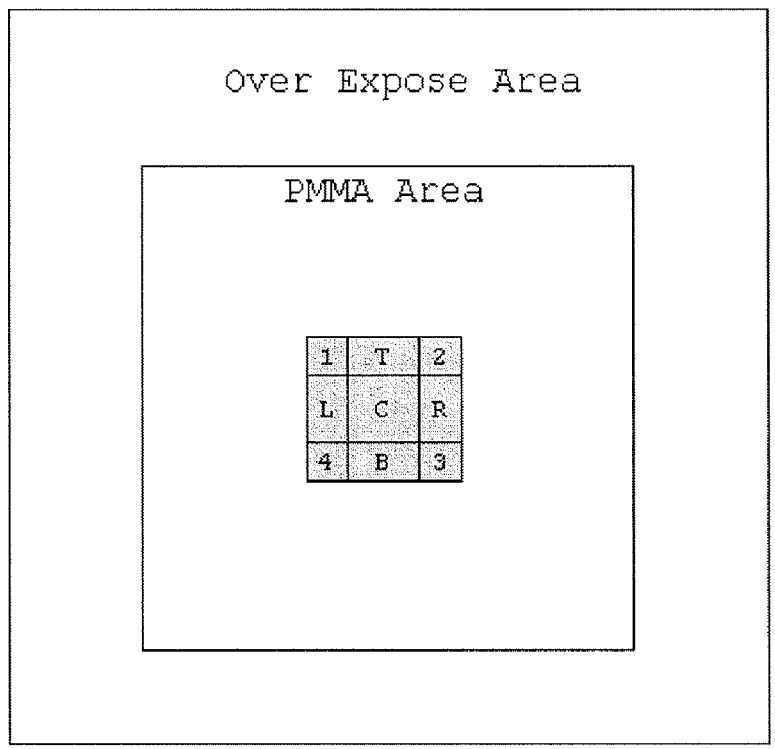
FIG. 3 is a composition schematic view of a typical X-ray object image for verifying the practical effect of the present invention.

In order to clearly show the practical effect of the present invention, a practical image is obtained after being processed by the "virtual grid" imaging system shown in FIG. 1, and then a series of comparison experiments is performed between the practical image obtained in the present invention and the image obtained by using a common grid (i.e., the anti-scatter grid disclosed in Chinese Patent NO. 02126906.8). The to-be-detected object is an organic glass (PMMA shown in the figure) with a size of 290×290×99 mm and a lead (Pb) with a size of 45×45×4 mm. The common grid for making comparison has the specification of: Size: 440× 480 mm, Line: 80L/CM, Ratio: 10:1, P.D: 150CM. The X-ray detector is a direct digital-imaging flat-panel detector. The lead (Pb) is attached at the center of the organic glass (PMMA) on the side close to the X-ray source, for blocking the straight X-rays, and the blocking area shall be a low brightness area with uniform density when no scattered rays exist. FIG. 3 is a composition schematic view of a typical X-ray object image for verifying the practical effect of the present invention, and the image can be divided into an over-exposure area, an organic glass (PMMA) area, and a lead (Pb) area. The lead (Pb) area is an area for blocking straight rays, in which the center portion is the portion having the lowest scattered rays, and generally, the four edges and four corners are easily polluted by the scattered rays. The experiment will analyze the density distribution of lead (Pb) protected area, and determines the pollution extent by measuring pixel values respectively for the center portion and the four edges and corners.

Figure 4A:
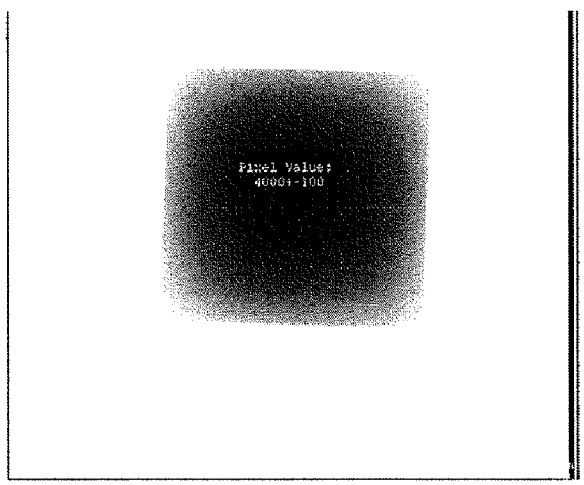
FIGS. 4(a) to 4(f) are graphic examples of different applications under an exposure condition of 45 kV.

Without using the common grid, under conditions of 45 kV, 75 kV, and 125 kV respectively, the dosage mAs is adjusted to make the brightness at the gray region of the organic glass of the image reaches a medium gray value (the gray value is about 8000). FIG. 4(a) shows pollution situation of scattered rays to Pb protected area under an exposure condition of 45 kV, and it can be seen from the figure that, the pollution at the four corners is most severe, the pollution at the four edges is less severe, and the pollution at the center is much lower.

Figure 4B:
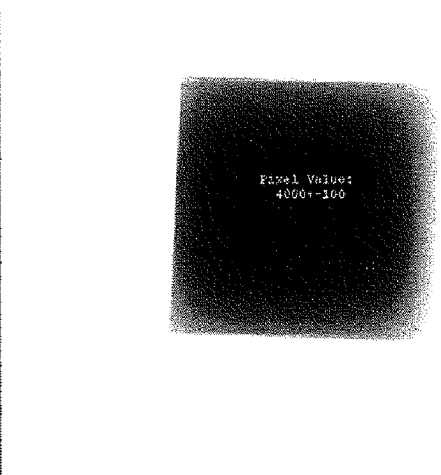

By using the common grid, under conditions of 45 kV, 75 kV, and 125 kV respectively, the dosage mAs is adjusted to make the brightness at the gray region of the organic glass of the image reach a medium gray value (about 8000) (only 5000 can be reached with the maximum dosage of 400 mAs under the conditions of Grid 45KV). FIG. 4(b) shows the situation after adding the grid under the exposure condition of 45 kV, and it can be seen that, the pollution caused by the scattered rays at the four edges and four corners is significantly reduced. However, the required dosage of the rays is 2.5 times of the dosage when the common grid is not used, and the required dosages under various conditions are recorded in the experiment, see Table 1.

TABLE 1

|  | Without Grid or Using Virtual Grid | | | Using Common Grid | | |
| --- | --- | --- | --- | --- | --- | --- |
| kV | 45 kV | 75 kV | 125 kV | 45 kV | 75 kV | 125 kV |
| mAs | 160 mAs | 16 mAs | 3.2 mAs | 400 mAs | 40 mAs | 8 mAs |
| Ray Dosage in Organic Glass Area | 156 uGy | 84 uGy | 62 uGy | 397 uGy | 218 uGy | 154 uGy |
| Gray Value in Organic Glass Area | 7000-8000 | 7000-9000 | 7000-9000 | 4000-5000 | 6800-7600 | 7800-9100 |
| Gray Value in Lead Area | 4000-4500 | 4750-5300 | 5100-5600 | 500-1000 | 1800-2300 | 3200-3800 |

Figures 4C, 4D:
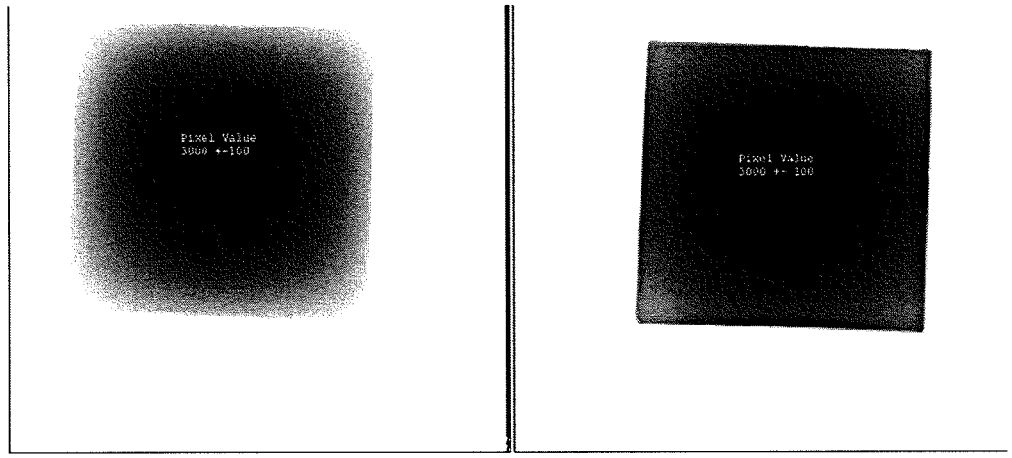

FIGS. 4(c) and (d) are respectively an original image and an image obtained after inhibiting the pollution of the scattered rays through utilizing the present invention under the same exposure condition (45 kV). Comparing FIG. 4(d) with FIG. 4(c), the scattered rays are significantly inhibited.

Figures 4E, 4F:
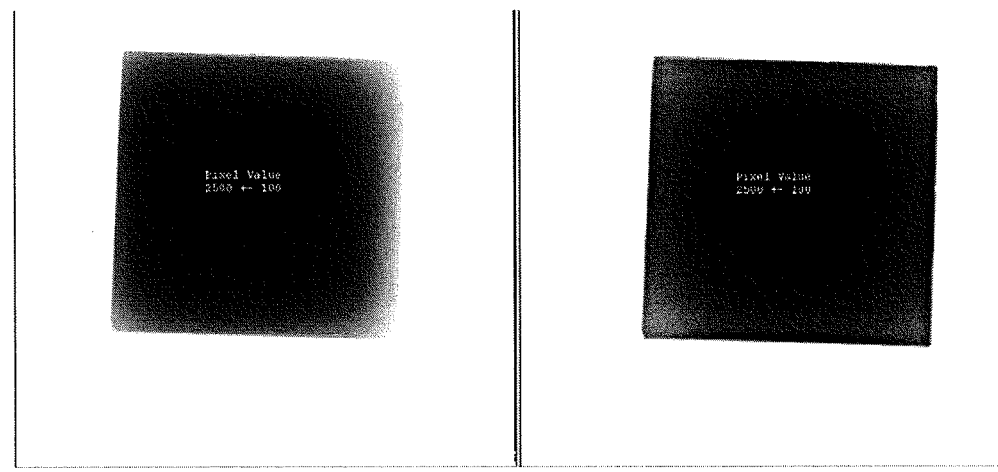

FIG. 4(e) shows an image after inhibiting the scattered rays by using the common grid, and FIG. 4(f) shows an image after inhibiting the scattered rays by using the "virtual grid" provided by the present invention, and it can be seen that, the scattered rays are significantly inhibited in two figures. The inhibition of the scattered rays at the four edges and corners using the "virtual grid" is better than that using the common grid.

Figure 5A:
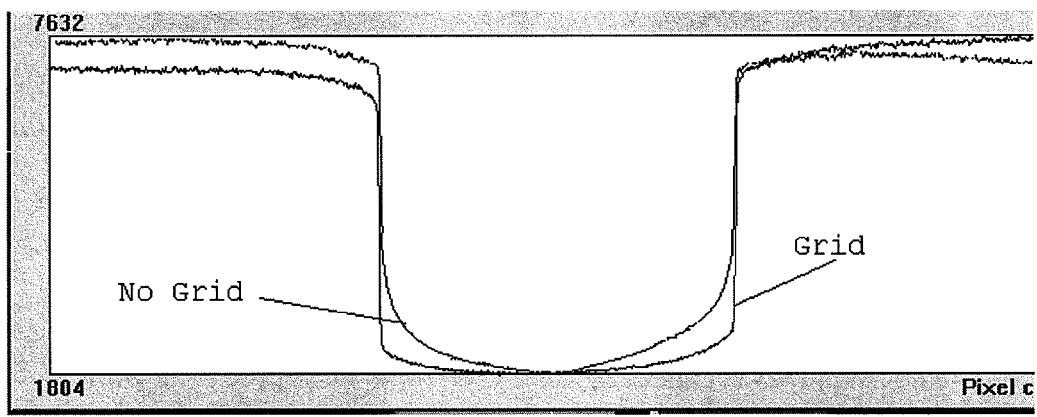
FIGS. 5(a) and 5(b) are density curve comparison diagrams under 75 kV, in which grid represents common grids, and V-grid represents virtual grids.
Figure 5B:
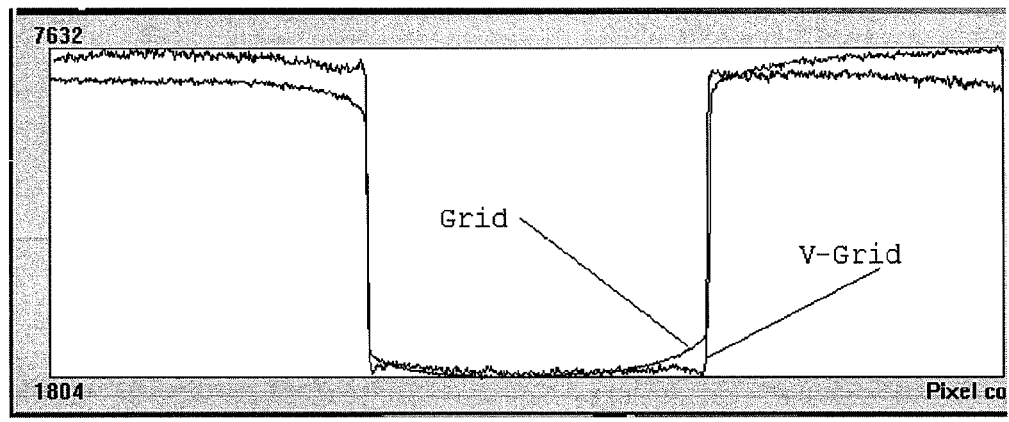

FIGS. 5(a) and 5(b) are density curves of the original image, the image using the common grid and the image using the "virtual grid" under the same kV condition respectively. In FIG. 5(a), the pixel value of Pb protected portion is about 1800, and the pixel value of the portion without being protected by Pb approaches 8000. The pollution of the scattered rays causes the pixel value at the edge of the Pb protected portion to be increased, and it indicates that, the farther the portion is away from the bottom center, the more serious the pollution is. After applying the common grid, the curve drops down at two bottom corners, which is much closer to the bottom compared with the curve without using the grid. The density curve in FIG. 5(b) shows that the curve of the "virtual grid" can be substantially fitted with that of the common grid, and the inhibition of the scattered rays at the four edges and corners is preferred than that of the common grid.

Figure 6A:
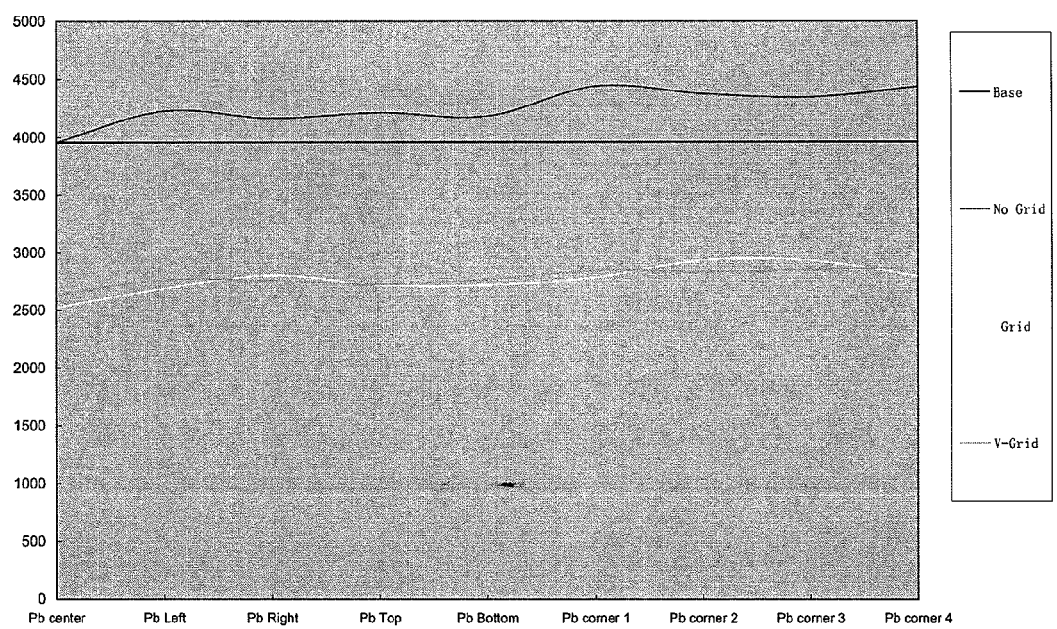
FIGS. 6(a), 6(b) and 6(c) are density statistic curves respectively under exposure conditions of 45 kV, 75 kV and 125 kV.
Figure 6B:
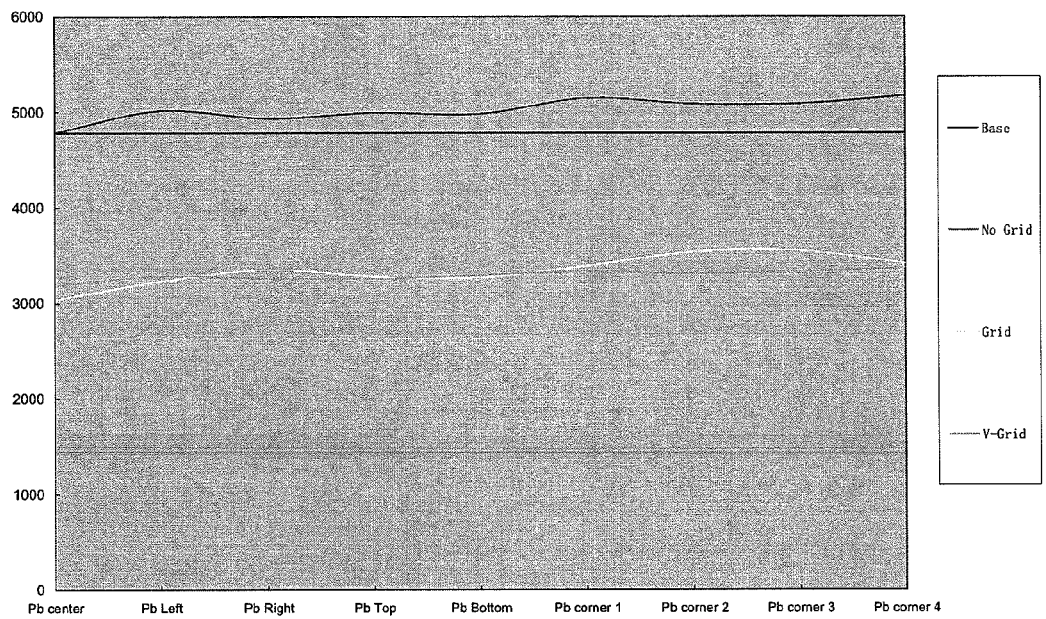
Figure 6C:
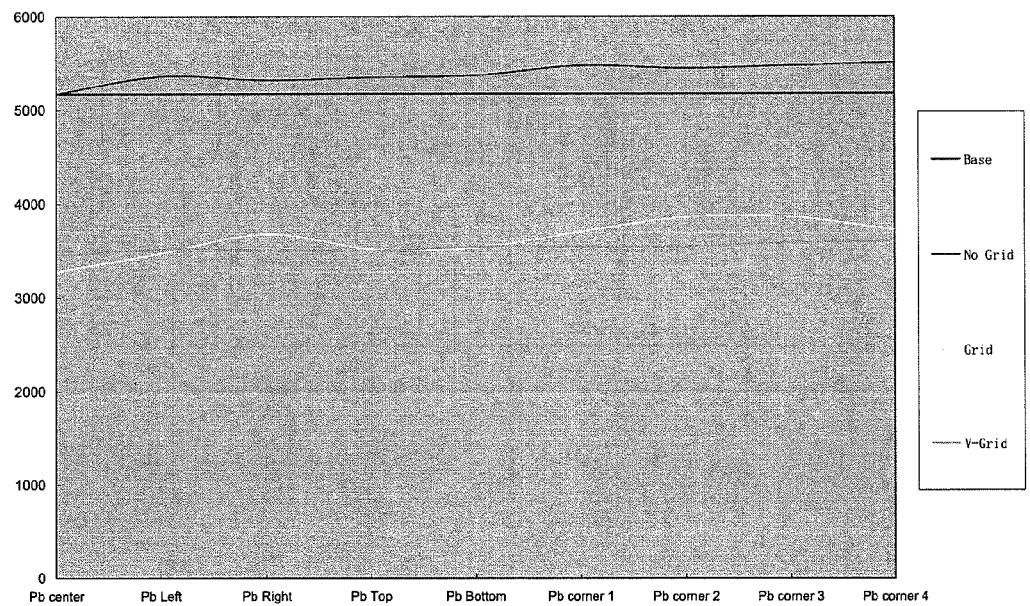

FIGS. 6(a), 6(b) and 6(c) are density statistic curves of lead (Pb) protected area under exposure conditions of 45 kV, 75 kV and 125 kV. By statistically comparing the central area, edge area and corner area of the lead (Pb) protected area, it can be seen that, in the density curve of the "virtual grid", the density at the center of the lead (Pb) protected area is close to that of the four edges and four corners, and the curve is approximately straight, which is most close to the parallelism of the Base line, indicating that the "virtual grid" has the most obvious effect for inhibiting scattered rays.

In practical use, in the "virtual grid" imaging system shown in FIG. 1, in order to increase the image processing speed, an exclusive nonlinear lookup table can be stored in the virtual grid unit 9. When performing an operation requiring a large number of calculations such as decomposing the image, a mapping process through the nonlinear lookup table can be directly used to achieve the de-scattering, enhancement and de-noising processes, which is helpful for achieving the real time process of the image. The relevant mapping curves are realized by Equation (12):

$$Sigm(x) = a \times \frac{S(g \times (x-m)) - S(-g \times (x-m))}{S(g) - S(-g)} + b, \quad (12)$$

wherein $$S(x) = \frac{1}{1 + e^{-x}},$$

by adjusting parameters a and b, the output range of the curve is adjusted, and by adjusting parameters g and m, the slope and shift of the curve are adjusted. Here, a, b, g, and m are all mapping relation data that are calculated previously, and curve parameters determined when mapping the curve are fitted according to the mapping relation data. In the present invention, corresponding curves can be previously fitted respectively for the de-scattering, enhancement and de-noising processes of each layer in the pyramid decomposition, so as to generate the lookup table required in the calculation. In practical process, fast processing can be realized by directly using the lookup table.

The virtual grid imaging method for eliminating scattered radiation effect and the system thereof have been illustrated in detail. For those of ordinary skill in the art, any obvious modifications to the present invention without departing from the spirits of the present invention shall be considered as infringement to the patent rights of the present invention, and shall bear corresponding legal liability.

What is claimed is:

1. A virtual grid imaging method for eliminating scattered radiation effect, applicable for imaging with high energy rays, wherein scattered rays reaching a surface of a detector are not filtered, data of scattered rays and straight rays are all sampled, and then separation and inhibition for the scattered ray component are performed for the sampled data, comprising:
    (1) decomposing a digital image generated by high energy rays into multi-band images from high to low according to frequencies;
    (2) directly performing de-scattering process for low-frequency band images;
    (3) performing contrast enhancement process for high-frequency band images;
    (4) merging the images of various frequency bands processed in the step (2) and the step (3), and forming an output image.

2. The virtual grid imaging method for eliminating scattered radiation effect as claimed in claim 1, wherein:
    in the step (1), the digital image is decomposed by means of Laplacian Pyramid decomposition.

3. The virtual grid imaging method for eliminating scattered radiation effect as claimed in claim 2, wherein:
    in the step (1), the number of layers n decomposed from the digital image meets the following equation:

$n=\log(N)/\log(2)-0.5$, wherein N is the size of the digital image.

4. The virtual grid imaging method for eliminating scattered radiation effect as claimed in claim 1, wherein:
in the step (1), the digital image is decomposed by means of Wavelet Transform.

5. The virtual grid imaging method for eliminating scattered radiation effect as claimed in claim 4, wherein:
in the step (1), the number of layers n decomposed from the digital image meets the following equation:

$n=\log(N)/\log(2)-0.5$, wherein N is the size of the digital image.

6. The virtual grid imaging method for eliminating scattered radiation effect as claimed in claim 1, wherein:
in the step (2), the de-scattering process is performed for the low-frequency band images according to the following equation: $C_k(x,y)=\text{Gain}(L_k(x,y),k) \times L_k(x,y)$,
wherein $\text{Gain}(L_k(x,y),k) \in [0,1]$ is a function in positive correlation with image brightness and frequency band, $C_k(x,y)$ is the low-frequency band images after being processed, $L_k(x,y)$ is the low-frequency band images obtained from decomposition in the step (1), and K is a positive integer.

7. The virtual grid imaging method for eliminating scattered radiation effect as claimed in claim 1, wherein:
in the step (3), the contrast enhancement process is performed for the high-frequency band images according to the following equation:

$E_k(x,y)=\text{Sigm}(L_k(x,y),k) \times L_k(x,y)$ wherein $\text{Sigm}(L_k(x,y),k)$ is an S-type nonlinear amplification function, in inverse correlation with contrast of pixel, $E_k(x,y)$ is the high-frequency band images after being processed, $L_k(x,y)$ is the high-frequency band images obtained from decomposition in the step (1), and K is a positive integer.

8. The virtual grid imaging method for eliminating scattered radiation effect as claimed in claim 1, wherein:
in the step (4), an interpolation frequency up-conversion sampling is performed for the lowest frequency band image after being processed in the step (2), and then, the image is overlapped with an adjacent image of a higher frequency band through Gaussian convolution interpolation process, so as to generate a new image of a higher frequency band, and the same process is performed upwards layer by layer, until a processed image of a size identical to the original image is obtained.

9. The virtual grid imaging method for eliminating scattered radiation effect as claimed in claim 1, wherein:
in the step (4) or after the step (4), de-noising process is performed for the image according to the following equation:

$f_k(x,y)=(1-b) \times R_k(x,y)+b \times T_{k+1}(x,y)$ wherein $b=\text{Weight}(T_{k+1}(x,y),k)$ is in positive correlation with image brightness and frequency band, $R_k(x,y)$ is an image of the $K^{th}$ frequency band, $T_{k+1}(x,y)$ is an image of the $(K+1)^{th}$ frequency band after performing interpolation frequency up-conversion sampling process, and $f_k(x,y)$ is an image of the frequency band output after performing the de-noising process, and K is a positive integer.

10. The virtual grid imaging method for eliminating scattered radiation effect as claimed in claim 1, wherein:
data required during the image processing is compiled in advance, and corresponding mapping curves are fitted, such that when performing image processing, the required data is obtained quickly by directly using a mapping process through a lookup table.

11. The virtual grid imaging method for eliminating scattered radiation effect as claimed in claim 1, wherein:
the high energy rays comprise, but not limited to, X-rays or gamma rays.

12. A virtual grid imaging system for eliminating scattered radiation effect, wherein:
the virtual grid imaging system comprises a high energy ray emitting unit, a high energy ray detecting unit, an image acquiring, pre-processing and correcting unit, a virtual grid unit, an image post-processing unit, and an image displaying unit, wherein the high energy ray emitting unit emits high energy rays that penetrate through a to-be-detected object and then received by the high energy ray detecting unit to generate a digital image; the high energy ray detecting unit, the image acquiring, pre-processing and correcting unit, the virtual grid unit, the image post-processing unit, and the image displaying unit are connected in sequence; and after the virtual grid unit performs the process as claimed in claim 1, the image with scattered radiation effect being eliminated is sent to the image displaying unit to be displayed.

13. The virtual grid imaging system for eliminating scattered radiation effect as claimed in claim 12, wherein
the high energy ray emitting unit is an X-ray tube, and the high energy ray detecting unit is an X-ray detector.

* * * * *